United States Patent [19]
Gerig

[11] Patent Number: 5,897,520
[45] Date of Patent: Apr. 27, 1999

[54] UNITARY DORSAL NIGHT SPLINT

[75] Inventor: Bradley Gerig, Indianapolis, Ind.

[73] Assignee: Active Ankle Systems, Inc., Louisville, Ky.

[21] Appl. No.: 08/764,292

[22] Filed: Dec. 12, 1996

[51] Int. Cl.⁶ .................................................. A61F 5/00
[52] U.S. Cl. .............................. 602/527; 602/23; 602/28; 602/65
[58] Field of Search ................................... 602/20, 21, 23, 602/24, 26, 27, 28, 29, 60, 61, 62, 65, 5, 6; 128/881, 882

[56] References Cited

U.S. PATENT DOCUMENTS

| | | | |
|---|---|---|---|
| 3,504,668 | 4/1970 | Boudon | 602/28 |
| 3,916,886 | 11/1975 | Rogers | 602/28 |
| 4,446,856 | 5/1984 | Jordan | 602/27 |
| 5,125,400 | 6/1992 | Johnson, Jr. | 602/27 X |
| 5,219,324 | 6/1993 | Hall | 602/28 |
| 5,259,834 | 11/1993 | Wittmeyer | 602/28 |
| 5,269,748 | 12/1993 | Lonardo | 128/882 X |
| 5,441,015 | 8/1995 | Farley | 602/27 |
| 5,501,659 | 3/1996 | Morris et al. | 128/882 X |
| 5,507,720 | 4/1996 | Lampropolous | 602/27 |
| 5,520,628 | 5/1996 | Wehr | 602/27 |
| 5,609,568 | 3/1997 | Andrews | 602/28 |
| 5,776,090 | 7/1998 | Bergmann et al. | 602/28 |

FOREIGN PATENT DOCUMENTS

| | | | |
|---|---|---|---|
| 3300111 | 7/1984 | Germany | 602/29 |

Primary Examiner—Richard J. Aplay
Assistant Examiner—Kim M. Lee
Attorney, Agent, or Firm—Middleton & Reutlinger; John F. Salazar

[57] ABSTRACT

The Dorsal Night Splint orthosis for human wearers includes a substantially rigid upright member consisting of an upper portion and a lower portion. When placed upon the foot of the wearer, said upper portion proceeds downward from approximately beneath the knee to the lower portion which terminates at the top of the foot. The lower portion is further defined by two opposed ankle splints. Said opposed ankle splints extend downward on each side of the ankle and wrap around, overlap and terminate at the Plantar aspect of the foot. A flexible member is positioned between the wearer and the upright member to provide padding for extended wearing of the device. The device is fastened to the wearer by one or more Velcro straps. When correctly placed upon the foot, the heel and the attachment of the Achilles tendon, as well as the wearer's toes, remain exposed. This device is designed to be a supplemental form of treatment that, when worn at night or during extended periods of inactivity can, in conjunction with traditional treatment, significantly reduces the recovery time in the treatment of plantar fasciitis, acute ankle sprains, achilles tendon repair, foot drop, or any other condition or injury that would cause heel cord/Achilles tendon shortening in patients during periods of bed rest or when ankle immobilization is desired.

9 Claims, 5 Drawing Sheets

UNITARY DORSAL NIGHT SPLINT

FOOT ORTHOTICS, BACKGROUND OF THE INVENTION (1) Field of the Invention

This invention relates to a supplemental treatment for Plantar Fasciitis, Acute ankle sprains, acute gastrocnemius strains, achilles tendon repair, injury, foot drop, or any other condition or injury that would cause heel cord/Achilles tendon shortening in patients during periods of bed rest or when ankle immobilization is desired. The subject invention promotes and speeds the healing process when used in conjunction with more traditional treatments.

(2) Description of the Prior Art

In the general area of orthotic splints, prior art has been developed mostly in the area of walking type splints wherein inventors have concentrated on the development of such splints or braces which may be worn by the human in a concealed manner by being placed inside of the trousers and installed into conventional type non-orthotic shoes. Such representative type devices are: U.S. Pat. No. 4,559,934 to Phillip dated Dec. 24, 1985, U.S. Pat. No. 5,219,324 to Hall dated June 15, 1993, and U.S. Pat. No. 3,504,668 to Boudon dated Apr. 7, 1970.

The instant invention is meant to be worn at night or periods of rest wear the wearer is not placing pressure or weight on the effected foot/ankle. Prior art in this area is represented by U.S. Pat. No. 5,399,155 to Strassburg et al. dated Mar. 21, 1995. This device is designed to accomplish substantially the same results as the subject invention; however, it is our belief that the subject invention has some distinctive advantages.

The Strassburg device is for the most part a sock with a tensioner type strap attached to the toe and upper portion thereof The tension placed on the ankle may be varied by lengthening or shortening said tension strap. Many wearers have complained that this type of device is uncomfortable when sleeping with bed linen or covers over the effected foot due to the weight of the covers exerting a downward force upon said tension strap thereby placing a surplus of weight upon the effected ankle. During the summer months of the year or in any particularly warm climate (or in cases where bed linens are placed over the device) the wearing of the sock proved too warm for the wearer. The design of the Strassburg device also does little to prevent the side to side motion of the foot in relation to the ankle. The aforementioned design also does not allow for the foot to be positioned and retained at an exact posture due to the flexible nature of the tension strap.

The subject invention addresses and solves the aforementioned problems of the Strassburg device and like devices. The subject invention provides for a predetermined positive displacement of the foot in relation to the ankle. The wearer does not have to wear any type of sock or undergarment when wearing the subject invention thereby alleviating the heat problem associated with the Strassburg device. The subject invention also allows the posterior side of the lower leg, ankle, foot, and toes to remain substantially exposed while being worn. This substantial exposure provides the wearer with an effective compact device which allows the wearer to enjoy substantial freedom of movement of the effected extremity while still maintaining the desired immobilizing effect.

The subject invention, when worn as prescribed, places the plantar aproneurosis in an immobilized position. While this immobilized position is not sufficient to create to lengthening effect on the aproneurosis, it is of sufficient force so as to prevent it from contracting. This is achieved by holding the ankle and forefoot joints in a position of slight dorsiflexion and preventing the ankle and forefoot joints from adopting a position of plantarflexion. In this way, the plantar aproneurosis is not allowed to contract during the period that the subject invention is being worn. The effect is that after removal of the subject invention by the wearer, and upon bearing weight on the effected foot, the plantar aproneurosis will not be placed in pathologic tension thus reducing and/or eliminating pain. The subject invention may also be utilized to immobilize the ankle for any diagnosis or condition where a neutral position is desired.

Summary of the Invention

The subject invention is directed to an anterior dorsal ankle foot orthopedic splint to be used as a supplemental form of treatment that, when worn by humans at night or during extended periods of inactivity can, in conjunction with traditional treatment, significantly reduce the recovery time in the treatment of plantar fasciitis, acute ankle sprains, achilles tendon repair, foot drop, or any other condition or injury that would cause heel cord/Achilles tendon shortening in patients during periods of bed rest or when ankle immobilization is desired.

Specifically, the splint of the subject invention includes a substantially rigid upright member which is further defined as having an upper portion and a lower portion which are adapted to be placed in an anterior position extending generally from the dorsal portion of the foot along the shin to a point below the knee. The base of the foot is carried and supported by a split base portion and opposed ankle splints respectively. Said opposed ankle splints project downward from the lower portion of the upright member which is positioned upon the dorsal portion of the foot. Said opposed ankle splints extend downward and wrap around each side of the medial and lateral aspect of the ankle. Said opposed ankle splints overlap each other and terminate under the Plantar aspect of the foot thus forming a split base portion. In the preferred embodiment, the split base portion, positioned under the foot, extends from slightly in advance of the heel to the toes of the wearer. Although the split base portion and the opposed ankle splints are constructed of a substantially rigid material, said portions remain flexible enough to permit adjustment of the split base portion and the opposed ankle splints (by adjusting the tension of the lower support strap) whereby said portions substantially conform with the wearer's foot width thereby providing for a snug fit whereby the desired level of immobility of the wearer's foot is achieved. For extended wearing and comfort, the subject invention is fitted with a flexible member which resides between the wearer and all portions of the upright member which contact the wearer, including: the splint base portion, the upper portion, the lower portion, and the opposed ankle splints. When properly placed upon the foot, the following remain exposed: the heel, the Achilles tendon, the toes, and a substantial portion of the posterior lower leg depending on the number and size of upper support straps being utilized. The preferred embodiment shows the subject invention having two upper support straps incorporated into the upper portion and one lower support strap incorporated into the lower portion. Securing the device to the wearer could easily be accomplished with any suitable number and size of support straps employing various fastening means. Of course the hook and loop type fastener (Velcro) permits quick installation and removal of the splint.

The subject invention is fitted to the wearer by sliding his or her foot through the yoke which is defined by the posterior side of the lower portion, the inward facing sides of the opposed ankle splints, and the inward facing sides of the split base portion until the flexible member contacts the wearer's leg. The upper support straps are then secured around the posterior portion of the wearer's lower leg in a snug manner which is not overly tight as to cause discomfort or a substantial loss of blood circulation. The lower support strap is secured around the opposed ankle splints and split base portion. As described in detail, the lower support strap is then used to adjust the support of the opposed ankle splints and split base portion to the width of the wearer's foot. The splint may be customized to fit each particular patient; however, it has been found that standard form splints are widely adaptable to a variety of patient needs and conditions, thereby reducing the cost of the splint to the patient where desired.

It is, therefore, an object and feature of the subject invention to provide an orthopedic splint to be used as a supplemental form of treatment that, when worn by humans at night or during extended periods of inactivity can, in conjunction with traditional treatment, significantly reduce the recovery time in the treatment of plantar fasciitis, acute ankle sprains, achilles tendon repair, foot drop, or any other condition or injury that would cause heel cord/Achilles tendon shortening in patients during periods of bed rest or ankle immobilization.

It is another object and feature of the subject invention to provide a lightweight splint which provides an anterior dorsal ankle foot orthosis supporting the foot in advance of the ankle.

The subject splint may be made in a simple and inexpensive molding or equivalent manufacturing procedure. As a result, it is comparatively inexpensive to effectively treat the diagnosed condition.

Other objects and features of the invention will be readily evident upon a study of the following specification and the accompanying drawings.

DETAILED DESCRIPTION OF THE PREFERRED EMBODIMENT

The following detailed description of the preferred embodiment is by way of example and not by way of limitation of the principals of the invention, and makes reference to the device represented in the figures.

Figure 1:
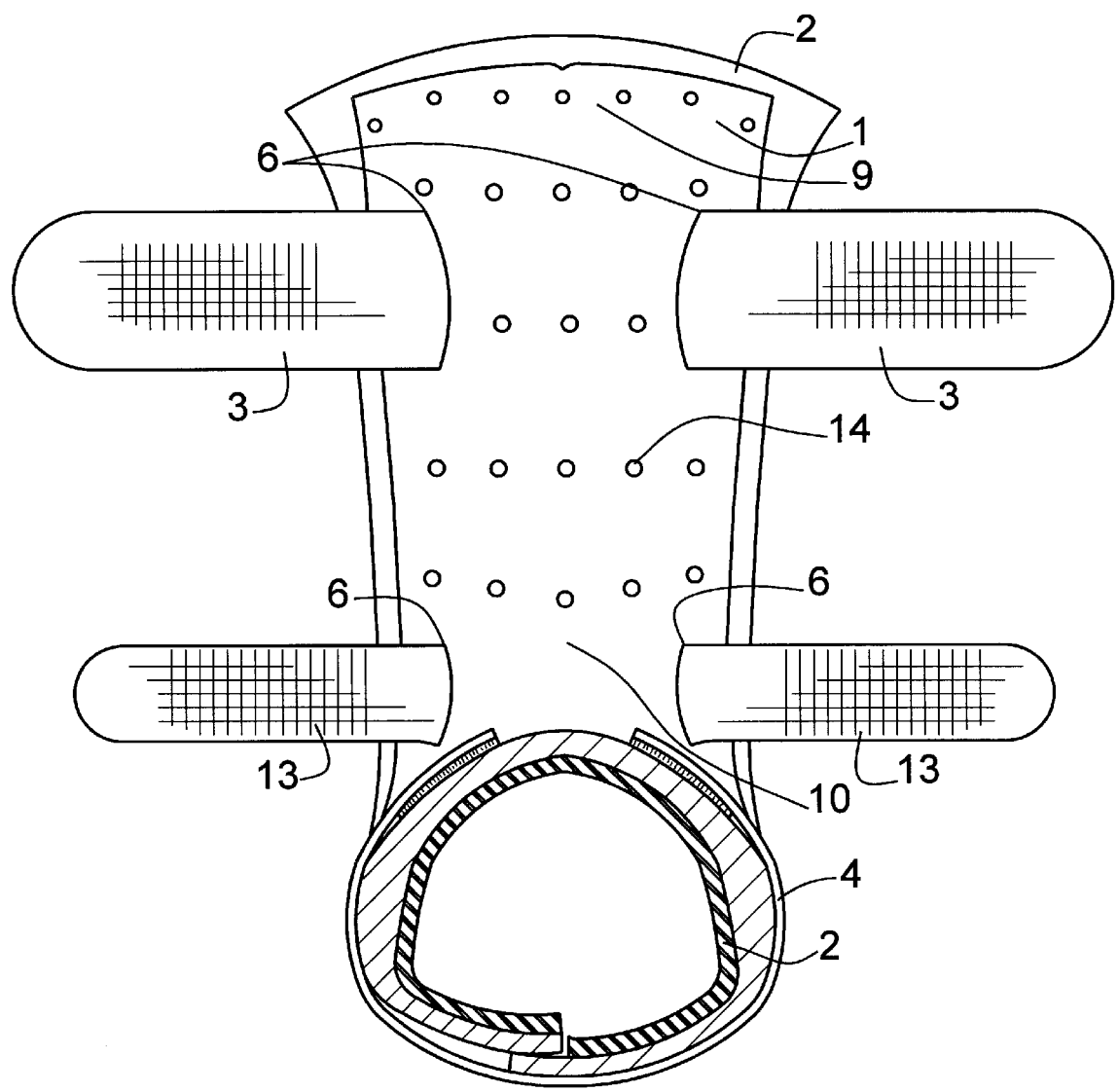
FIG. 1 is a anterior view of the dorsal night splint.
Figure 2:
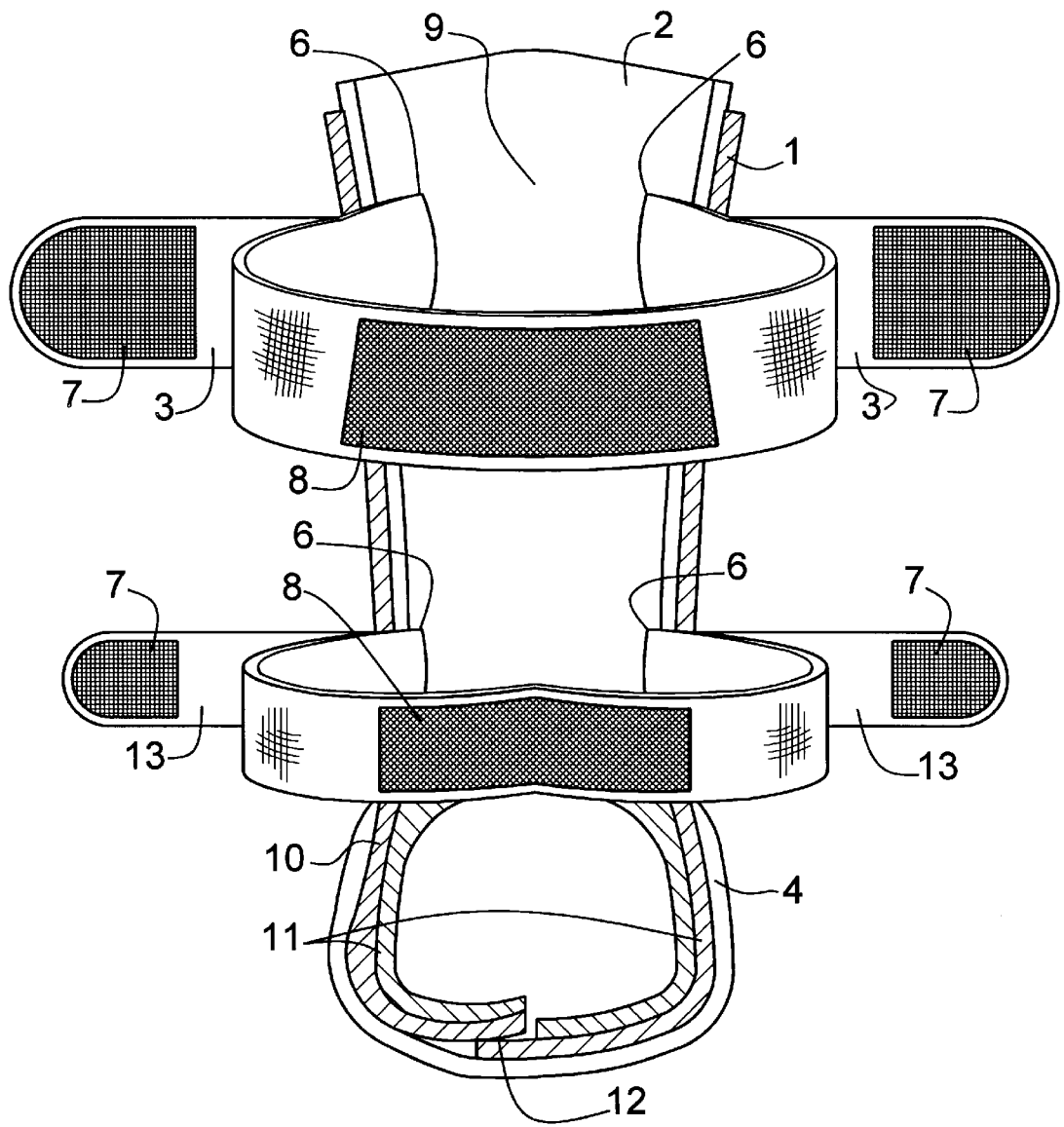
FIG. 2 is a posterior view of the dorsal night splint.

As shown in FIG. 1, the subject device is comprised of substantially rigid upright member 1 which conforms substantially with the dorsal portion of the wearer's foot along the shin to a point below the knee. Said upright member is defined as having an anterior and a posterior surface. FIG. 1 shows the subject device from the anterior view in a ready to wear position. The subject device is secured to the wearer's leg by a first and second upper support straps 3 and 13 respectively, and at least one lower support strap 4. Said upper support straps incorporate (FIG. 2) Velcro 7 and 8 (hook and loop type fasteners) thereupon which are affixed by stitch sewing, adhesive, or the like. Said upper support straps are installed into the upper portion 9 as illustrated in FIG. 2. As more clearly shown by FIG. 2, opposite ends of each upper support strap are inserted into the upper portion through opposed upper slots 6 from the posterior side of the subject device in a manner which allows each end of said upper support straps, which contain a hook type fastener 7 on opposite ends, to become engaged with and removably joined to a corresponding loop type fastener 8 which is also affixed thereto by sewing, adhesive or the like, and is substantially positioned in the middle of the same side as the hook type fastener 7 of each upper support strap 3. When the ends of each upper support strap containing the hook type fasteners 7 are pressed into the corresponding loop type fasteners 8, the upper support straps are removably fixed in a predetermined position by the wearer thereby securing the upper portion 9 to the wearer's leg.

Figure 3:
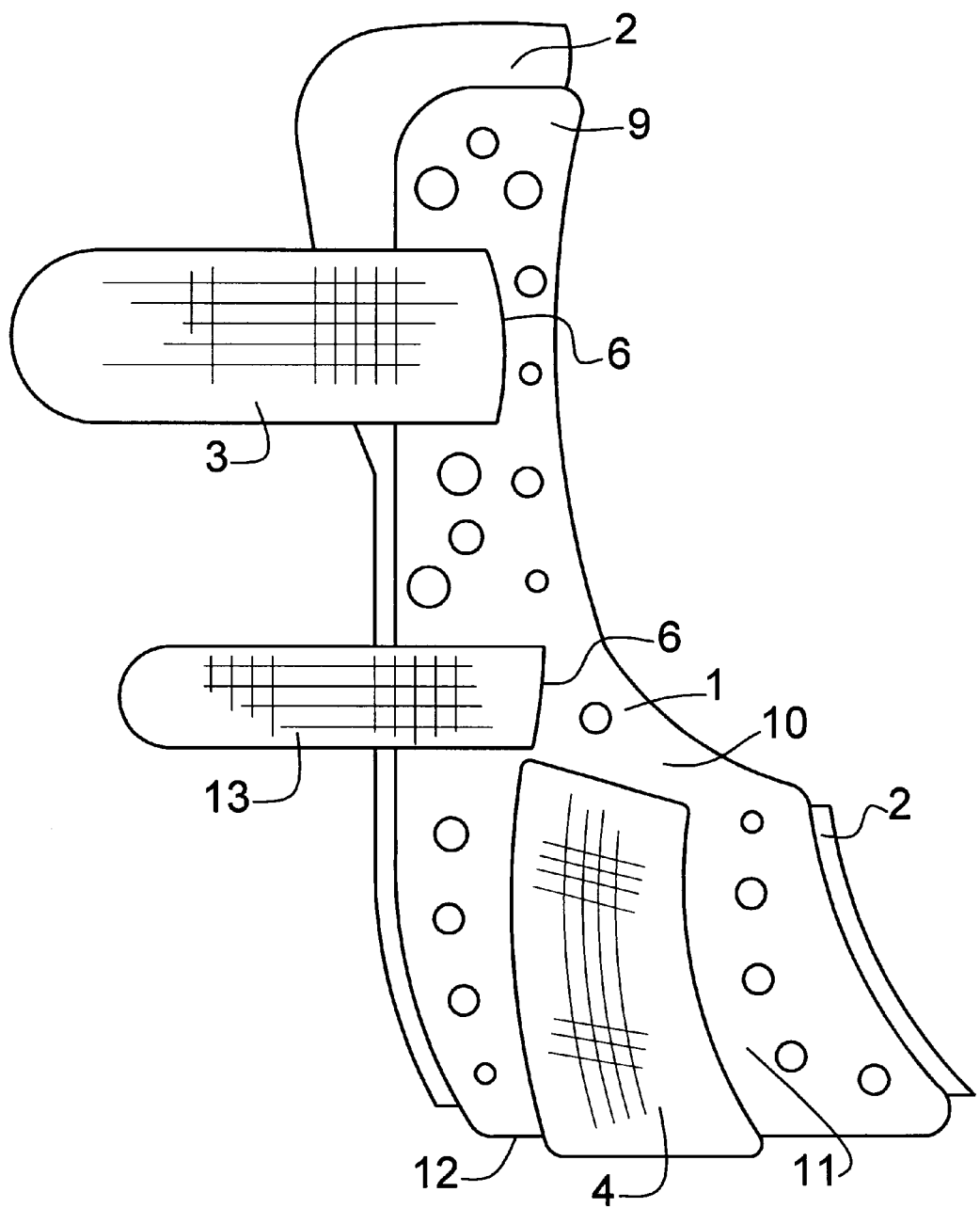
FIG. 3 is a side view of the dorsal night splint.
Figure 5:
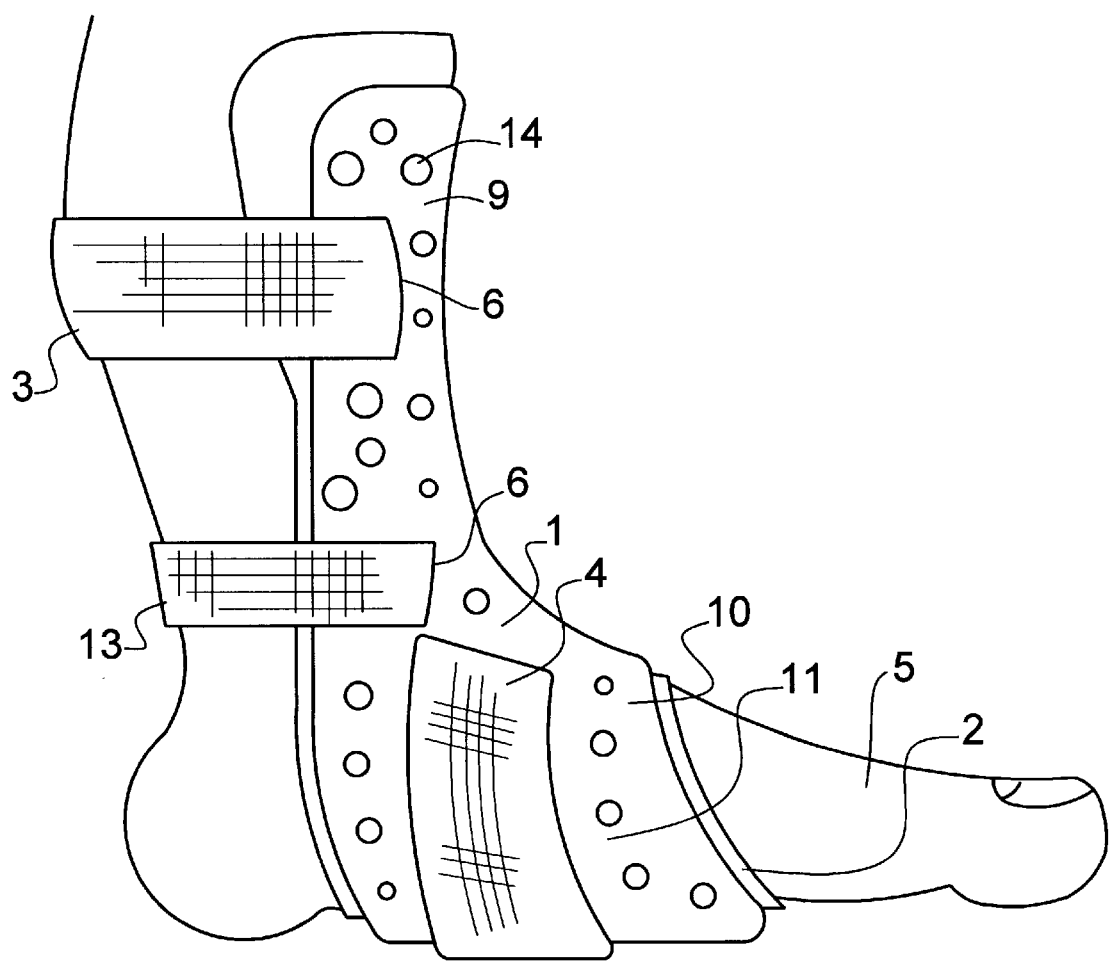
FIG. 5 is a side view of the dorsal night splint as worn by the wearer.

As shown in FIGS. 1, 3, and 5, the split base portion 12, positioned under the foot, extends from slightly in advance of the heel to the toes of the wearer. The lower support strap 4 is affixed to the lower portion 10 by Velcro (hook and loop type fasteners). The lower support strap 4 is wrapped around the opposed ankle splints 11 and the split base portion 12 with each end terminating at approximately the top of the lower portion 10. Although the split base portion 12 and the opposed ankle splints 11 are constructed of a substantially rigid material, said portions remain flexible enough to permit adjustment of the split base portion 12 (by adjusting the tension of the lower support strap 4) to substantially conform with the wearer's foot width. A predetermined level of immobilization is accomplished by said split base portion 12 and opposed ankle splints 11 being squeezably engaged by the aforementioned tension exerted by the lower support strap 4 thereby providing for a snug fit whereby the desired level of immobility of the wearer's foot is achieved. The amount of tension applied by the wearer to the lower support strap 4 when removably attached to the lower portion 10 determines the level of immobilization to the wearer's foot. At such time when the first upper support strap 3, the second support strap 13, and the lower support strap 4 are secured as described above, the subject device is then secured and in use by the wearer.

For purposes of this illustration, the ends of the upper support straps and the lower support strap contain a combination of hook and loop type fasteners. The hook and loop type fasteners which are affixed to said support straps are interchangeable with each other (by placing the loop fastener on ends and the hook fasteners in the middle of the upper support straps) as long as they are positioned substantially in the same manner as described above. Other fasteners not described herein are also acceptable to secure the upper portion 9 to the wearer. Employment of hook and loop type fasteners (Velcro) permits quick installation and removal of the splint. Typically, the upper support straps and the lower support strap are made of a flexible non-stretchable material such as nylon, cotton or the like.

For extended wearing and comfort, the subject invention is fitted with a flexible energy absorbing member 2 which resides between the wearer and all portions of the subject invention which contact the wearer, including: the inward facing sides of the splint base portion 12, the posterior side of the upper portion 9, posterior side of the lower portion 10, and inward facing sides of the opposed ankle splints 11. As shown is FIGS. 3 and 5, said flexible member 2 may be affixed to the posterior side of said upright member 1 by any conventional type of adhesive. Fixedly attaching said flexible member 2 to said upright member 1 is not crucial for the functional operation of the subject invention. When properly placed upon the foot, the following remain exposed: the heel, the Achilles tendon, the toes, and a substantial portion of the posterior lower leg depending on the number and size of upper support straps being utilized.

FIGS. 1, 3, and 5 show a plurality of optional apertures 14 which travel through the cross-section of the upright member which serve to lighten the subject invention along with providing a certain amount of ventilation to the anterior portion of the wearer's leg, including the foot, thereby providing a desired level of comfort.

As shown in FIG. 5, the subject invention is fitted to the wearer by sliding his or her foot through the yoke which is defined by the posterior side of the lower portion, the inward facing sides of the opposed ankle splints, and the inward facing sides of the split base portion until said flexible member contacts the wearer's leg. The upper portion is then secured around the posterior portion of the wearer's lower leg, by securing said upper support straps as described above, in a snug manner which is not overly tight as to cause discomfort or a substantial loss of circulation. The lower support strap is secured around the outwardly facing sides of the opposed ankle splints and split base portion. As described above in detail, the lower support strap is then used to adjust the support of the opposed ankle splints and split base portion to the width of the wearer's foot. The splint may be customized to fit each particular patient. However, it has been found that standard form splints are widely adaptable to a variety of patient needs and conditions, reducing the cost of the splint to the patient where desired.

Figure 4:
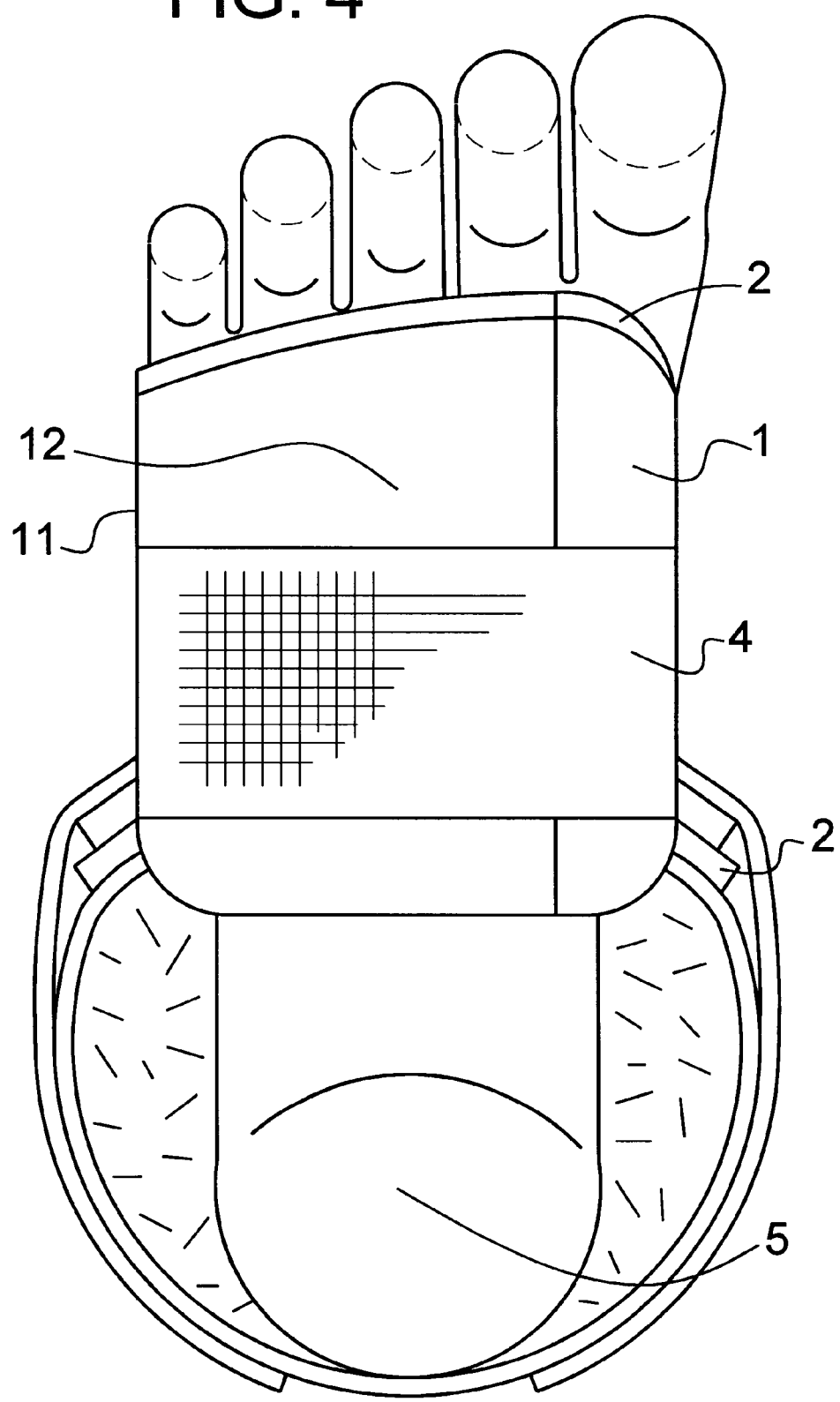
FIG. 4 is a bottom view of the dorsal night splint as worn by the wearer.

FIG. 4 shows a bottom view of the subject invention as placed upon the wearer. FIG. 5 shows a side view of the subject invention as placed upon the wearer. It is clearly shown from these two illustrations that the heel, Achilles tendon, toes, and a substantial portion of the posterior lower leg, depending on the number and size of upper support straps being utilized, remain exposed during use thereby providing an added level of comfort to the wearer.

While certain structural and functional characteristics of the subject invention have been shown and described in what is conceived to be the most practical and preferred embodiment, it is recognized that departures may be made respectively therefrom within the scope of the invention, which is not to be limited per se to those specific details as disclosed herein but is to be accorded the full scope of the claims so as to embrace any and all equivalent such devices, apparatus, and methods.

I claim:

1. An anterior dorsal foot orthotic device, comprising:
   an upper portion adapted to substantially engage only the anterior dorsal aspect of a patient's lower leg during use, said upper portion having a rigid upright member adapted to extend vertically along the anterior dorsal aspect of the patient's lower leg during use;
   a lower portion adapted to extend from the upper portion horizontally along the patient's foot during use, said lower portion defining two opposed ankle splints adapted to wrap around the medial and lateral aspects of the ankle of the wearer during use, said opposed ankle splints overlap each other and terminate under the plantar aspect of foot to define a split ortion to carry and support the foot during use;
   a flexible member secured to and extending along an interior surface of both said upper and said lower portions;
   an upper support strap removably attached to said upper portion to secure said upper portion to a wearer's lower leg; and a lower support strap removably attached to said lower portion to secure said lower portion around a wearer's foot.

2. The anterior dorsal foot orthotic device of claim 1 wherein said upper support strap further comprises a first and a second upper support strap and a plurality of opposed slots through which said first and said second upper support strap extends.

3. The anterior dorsal foot orthotic device of claim 2 wherein said first and said second upper support straps are of a hook and loop type fastener.

4. The anterior dorsal foot orthotic device of claim 1 wherein said rigid upright member and said opposed ankle splints farther comprise a plurality of apertures.

5. The anterior dorsal foot orthotic device of claim 1 wherein said split base portion extends from slightly in advance of the heel of said wearer to before the toes of said wearer.

6. The anterior dorsal foot orthotic device of claim 1 wherein said opposed ankle splints are comprised of a substantially rigid material.

7. The anterior dorsal foot orthotic device of claim 1 wherein said rigid upright member extends from the dorsal portion of the foot to a point below the knee of said wearer.

8. The anterior dorsal foot orthotic device of claim 1 wherein said flexible member is comprised of a soft energy absorbing material.

9. An anterior dorsal foot orthotic device, comprising:
   an upper portion and a lower portion, said upper portion extending vertically and said lower portion extending horizontally;
   said upper portion having a rigid upright member, said rigid upright member placed substantially on the anterior portion of the wearer's leg;
   said lower portion forming opposed ankle splints;
   a flexible member extending along an interior surface of said upper portion and said lower portion;
   an upper support strap removably attached to said upper portion to secure said upper portion to a wearer's leg;
   a lower support strap removably attached to said lower portion to secure said lower portion around a wearer's foot; and,
   wherein said opposed ankle splints overlap each other to form a split base portion which extends from slightly in advance of the heel of said wearer to before the toes of said wearer, said split base portio overlapping along the underside portion of the wearer's foot.

* * * * *

UNITED STATES PATENT AND TRADEMARK OFFICE
CERTIFICATE OF CORRECTION

PATENT NO. : 5,897,520
DATED : March 27, 1999
INVENTOR(S) : Bradley Gerig

It is certified that error appears in the above-identified patent and that said Letters Patent is hereby corrected as shown below:

Claim 1, col. 6, line 3, change "ortion" to --portion--;

Claim 4, col.6, line 24, change "farther" to --further--;

Claim 9, col. 6, line 57, change "portio" to --portion--

Signed and Sealed this

Fourteenth Day of December, 1999

Attest:

Q. TODD DICKINSON

Attesting Officer

Acting Commissioner of Patents and Trademarks